United States Patent [19]

Koffler

[11] Patent Number: 4,599,756
[45] Date of Patent: Jul. 15, 1986

[54] UNDERPAD HOLDER

[76] Inventor: Marshall N. Koffler, 8956 N.W. 9th Pl., Plantation, Fla. 33324

[21] Appl. No.: 731,456

[22] Filed: May 7, 1985

Related U.S. Application Data

[63] Continuation-in-part of Ser. No. 502,954, Jun. 10, 1983, abandoned.

[51] Int. Cl.$^4$ .......................... A47G 9/00; A61G 7/06
[52] U.S. Cl. ............................................. 5/484; 5/485
[58] Field of Search .................. 5/484, 485, 482, 487, 5/490; 604/358, 357, 356

[56] References Cited

U.S. PATENT DOCUMENTS 4,064,577 12/1977 Walters .................................. 5/484
4,391,010 7/1983 Kronman ................................ 5/484

FOREIGN PATENT DOCUMENTS 403237 10/1909 France .................................... 5/484

Primary Examiner—Alexander Grosz
Attorney, Agent, or Firm—Robert M. Schwartz; Edward I. Mates

[57] ABSTRACT

A plastic underpad holder, for use by generally incontinent patients has its ends secured to a mattress. The underpad holder having a rectangular frame to securely receive a disposable underpad to contain excess excretions. The underpad holder also has circular perforations providing ventilation to minimize heat build-up between the patient and the underpad holder.

4 Claims, 4 Drawing Figures

UNDERPAD HOLDER

RELATION TO OTHER APPLICATIONS

This application is a continuation-in-part of copending application Ser. No. 502,954, filed June 10, 1983 now abandoned, for Underpad Holder.

BACKGROUND OF THE INVENTION

1. Field of the Invention.

The present invention relates to a holder for disposable underpads for incontinent persons and is particularly suitable for use in hospitals. The underpads have the ability to contain excess excretion from an occupant of a bed and thus prevent the excretion from dirtying sheets and ruining mattresses.

2. Description of the Prior Art.

It is well known that persons confined to a bed, namely, incontinent persons, are often unable to control bodily excretions. Said excretions dirty sheets, causing the changing of sheets and a correspondingly higher frequency of laundering. These functions are labor intensive, are very expensive, and inconvenience the patient.

In addition, continued wetting of the sheets eventually causes the mattress to be ruined irrespective of plastic and/or rubber covers on the mattresses. This all caused undue and unnecessary economic hardships on hospitals and institutions as well as on individuals.

Prior to this invention, some solutions have been proposed to solve these problems. However, for one reason or another, these prior art proposals left something to be desired.

Industry has developed disposable underpads made of highly absorbent materials to collect the excretions. These disposable underpads generally come in several sizes. A problem with these pads is that they are moved around and become dislodged from under the patient thus defeating their intended purpose. The larger disposable pads covering a larger area are somewhat helpful in this respect; however, there is an increasingly and corresponding higher cost and they still move about the mattress. Today in hospitals and institutions, all means are being used to lower costs.

Therefore in practice hospitals and institutions order the smaller sizes to save money. At bedside however, the attendant will often use more than one disposable underpad to cover the mid-portion of the bed, because of the movements of the patient causing the underpad not to be in the right place at the right time. Of course, this procedure again causes waste.

U.S. Pat. No. 4,064,577, issued to Ronald D. Walters on Dec. 27, 1977, shows an improved bedding drawsheet having a textile base portion 26, large enough to tuck around and under the sides of a mattress 14, a panel 28 which is bonded to the base portion, and a removable moisture absorbent pad 32, attached to said panel 28 using VELCRO, registered trademark, attachment means. The latter attachment means provides bumps at least ⅛ inch thick which annoys a bed occupant. Furthermore, VELCRO ® attachment means must be applied in two strips along aligned elongated areas in the interfacial surfaces between the underpad and the underpad holder. It is an expensive and impractical technique to apply VELCRO ® attachment means in the precise alignment needed and also, it is difficult for hospital personnel to align the VELCRO ® means properly because one of the two strips to be aligned is always invisible to the person replacing a disposable underpad. In addition, the base portion 26 of the Walters device is of textile material that is too expensive to be disposable. Therefore, the textile base portion 26 must be laundered when dirty before it can be reused for another patient.

U.S. Pat. No. 3,646,624 to Frederick W. Zipf III issued on Mar. 7, 1972, discloses a plastic drawsheet 14 having an absorbent portion 22 secured by adhesive 24. Mr. Zipf's device does not easily accommodate changing of the water absorbent portion, if at all. Furthermore there is heat build-up caused by the plastic drawsheet. The present invention uses industry standard disposable underpads, which are quickly and easily changed without the need for adhesives.

French Pat. No. 403,237 to Vialard discloses a rubber pocket fully open in its upper median part so that a disposable absorbent cloth may be laid out flat between its edges and its bottom. However, Vialard requires a pair of safety pins at each of the four corners of the pocket to secure the cloth to the pocket. The use of pins is unacceptable under any patient in the medical field. Furthermore, the pins must be removed before a soiled disposable cloth can be removed from the pocket and a fresh cloth must be pinned to each corner of the Vialard pocket to be considered secured. Such pinning and unpinning is inefficient and annoying to hospital personnel.

Other methods show plastic sheets, which create a build-up of body heat causing the skin to break down resulting in decubitus ulcers forming on the patient's body. This is the result of a lack of air circulation. The present invention eliminates the heat build-up by placing openings in the base sheet to circulate air.

Other patents describing the closest subject matter provide for a number of more or less complicated features that fail to solve the problem in an efficient and economical way. None of these patents suggest the novel features of the present invention.

SUMMARY OF THE INVENTION

This invention relates to a novel underpad holder for use in combination with a disposable underpad and bedding mattress. The novel underpad holder needs no pins to secure the disposable underpad thereto and includes a thin continuous closed frame that is bonded at its outer edge portion to a plastic base sheet to maintain the latter in flat unwrinkled condition and has its inner edge portion free of any attachment or bonding to the plastic base sheet to define a peripherally extending uninterrupted inwardly facing groove between the inner edge portion of the frame and the plastic base portion. The outer portion of the groove is equal to or only a small fraction of an inch larger than the disposable underpad, so that the underpad may be inserted therein and the frame is sufficiently wide to cause its inner portion to overlap the disposable underpad sufficiently to maintain the underpad within the groove until a conscious force is applied to remove the underpad.

The groove is adapted to receive the perimeter portion of the disposable underpad and uses the weight of a patient occupying a bed to hold the underpad in flat unwrinkled condition under the thin frame without requiring any pins to maintain the underpad in position. The weight of the bed occupant keeps the inner frame peripheral portion in overlying relation over the peripheral portion of the disposable underpad until the incontinence of the occupant requires removal of the disposable underpad and its replacement. Neither unpinning nor pinning is required to replace a soiled underpad, nor is any thick attachment means that would annoy a bed occupant be needed with an underpad holder conforming to this invention.

It is the main object of this invention to provide an inexpensive and practical means to hold a disposable underpad in a place on a mattress without requiring any pinning or unpinning of the disposable underpad relative to the underpad holder or the use of attachment means between the disposable underpad and holder that is thick enough to annoy an occupant of the bed.

It is another object of this invention to provide each patient with a fresh underpad holder which can be re-used for that patient and then disposed.

It is yet another object of this invention to provide an underpad holder of the type described that also minimizes heat build-up under the body.

It is another object of this invention to provide an underpad holder that is easy to wipe down and clean.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention comprises the details of construction and combination of parts as will be more fully understood from the following description, when read in conjunction with the accompanying drawings in which.

DESCRIPTION OF THE PREFERRED EMBODIMENT

Figure 1:
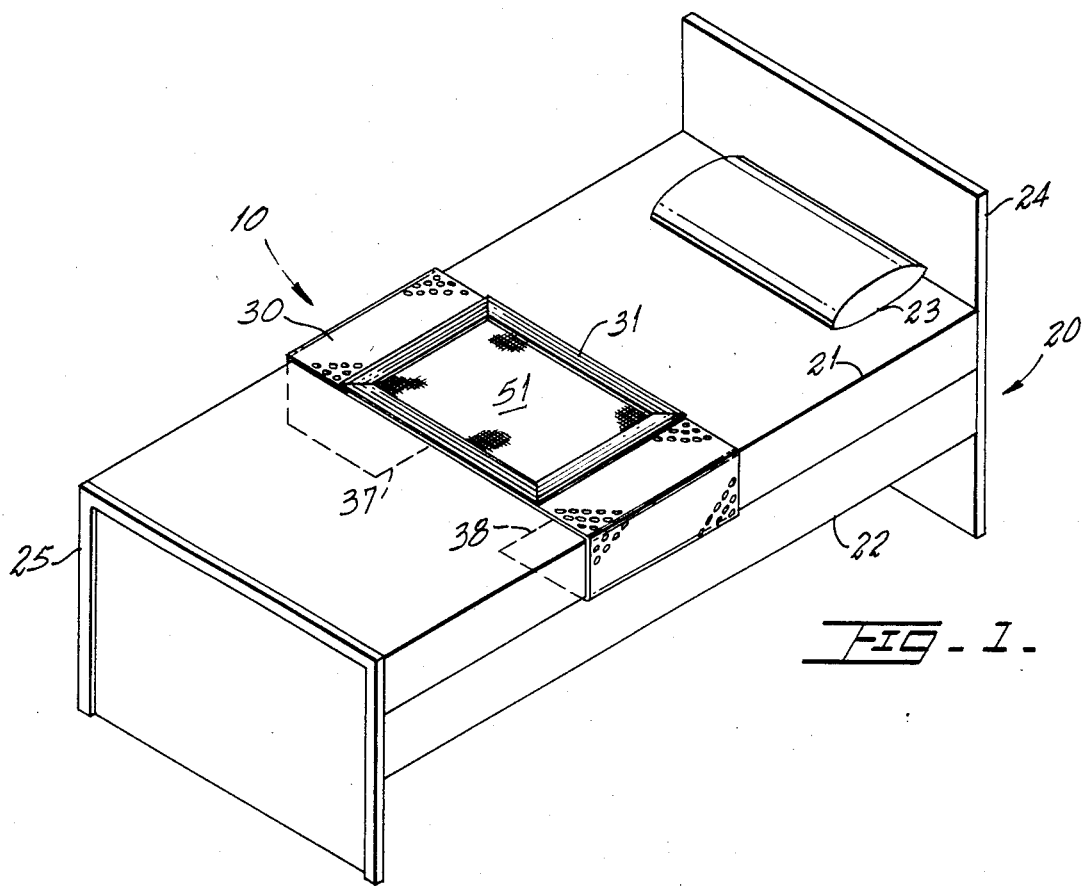
FIG. 1 is a perspective view of a bed and mattress provided with an underpad holder conforming to this invention.

Referring now to FIG. 1, where an underpad holder conforming to this invention is referred to generally as reference number 10, it can be seen that the underpad holder 10 has a length that traverses the width of bed 20. The latter includes a mattress 21, box spring 22, pillow 23, head board 24 and base 25.

Figure 2:
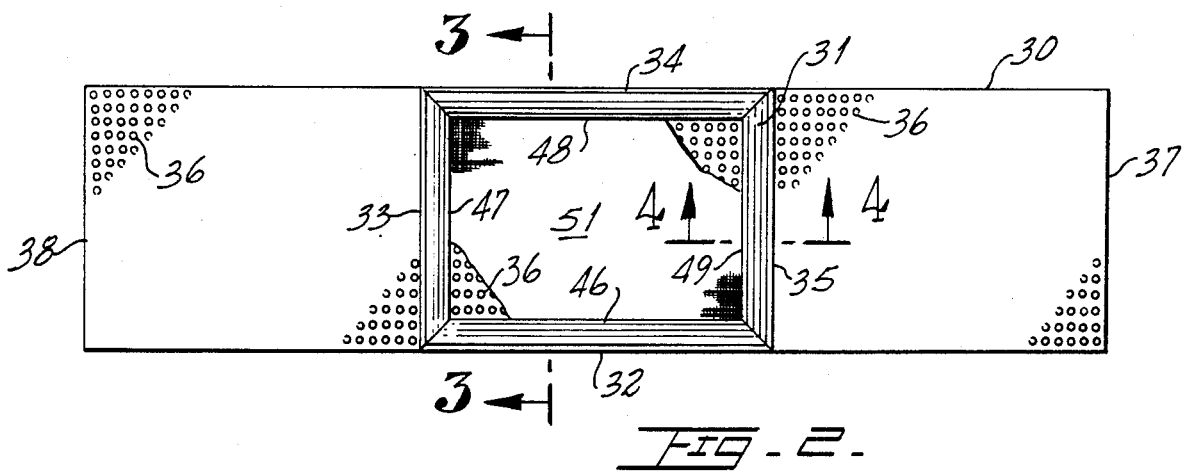
FIG. 2 is a top view of the underpad holder.

Referring to FIG. 2, the underpad holder 10 includes a base sheet 30 and a thin continuous rectangular frame 31 that is about one mil thick and two inches wide. The outside perimeter portion of frame 31 is bonded along a width of about ¼ inch to base sheet 30 along one-quarter inch wide edge at joints 32, 33, 34 and 35. The outer edge portion of frame 31 is bonded to the base sheet 30 using a standard heat process. Frame 31 has an inside perimeter consisting of elongated areas 46, 47, 48 and 49. The inside perimeter portion cooperates with base sheet 30 to form an inwardly facing uninterrupted peripheral groove about 1¾ inches wide. Base sheet 30 has a series of circular openings 36 allowing air to circulate, preventing heat build-up under the body when the underpad is used, namely between the plastic base sheet 30 and the patient and the bed.

Base sheet 30 extends from both ends of the frame, a distance laterally of the bed great enough such that the opposite sheet ends 37 and 38 can be securely tucked under the mattress 21. Other means not desirable to secure frame 31 to base sheet 30 can be used to secure the base sheet 30 to the underside of mattress 21 such as by pinning or taping.

Disposable underpads such as disposable underpad 51 are readily available in the market place by several vendors. These disposable underpads are made of highly absorbent materials, absorbing more than their weight. They are also manufactured in various sizes. The frames 31 are so sized relative to the underpads that the frame 31 overlaps at least 1½ inches of the perimeter of the underpad to insure keeping an underpad 51 within and below frame 31 without requiring any other fastening means such as pins or adhesive.

Figure 3:
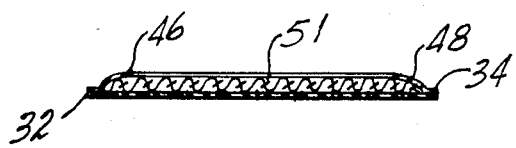
FIG. 3 is a section along lines 3—3 of FIG. 2 of the underpad holder and disposable underpad.

As can be seen in FIG. 3, frame 31 releasably secures a disposable underpad 51 relative to the base sheet 30 by receiving the marginal portion of said disposable underpad within said 1¾ inch wide, inwardly facing peripheral groove formed between the inside perimeter portion of frame 31 and base sheet 30. Said disposable underpad 51 is tucked in a flat unwrinkled arrangement below frame 31. The outside perimeter shown at edge joints 32 and 34 of frame 31 being slightly larger than the outside perimeter of the disposable underpad 51, and the inside perimeter of frame 31 shown at the inner margins of elongated areas 46 and 48 of frame 31 being smaller than disposable underpad 51, result in a flat, unwrinkled secure fit for the disposable underpad 51 on base sheet 30, within the inwardly facing peripheral groove.

Figure 4:
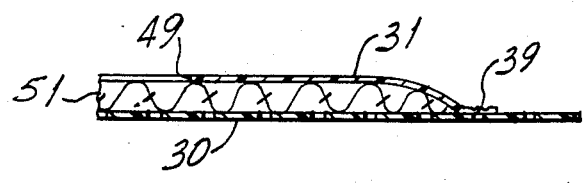
FIG. 4 is an exploded view along line 4—4 of FIG. 2, showing the frame, base sheet and disposable underpad.

FIG. 4 shows the disposable underpad 51 held in place by frame 31. It can now be noted that the outside perimeter of frame 31 shown at loci 39 along edge joint 35 is bonded to base sheet 30 leaving the remainder of frame 31 free from any bond to base sheet 30 to form the groove that receives the edges of disposable pad 51 in such a secure manner that no pinning or other attachment is needed to maintain underpad 51 in flat, unwrinkled relation when tucked therein as shown.

The nature of the underpad holder 10 makes it a necessity that it be easy to clean and be accessible to all parts. The patient can roll over far enough while remaining in the bed to all parts. The patient can roll over far enough while remaining in the bed to allow cleaning of base sheet 30 and insertion of a new disposable underpad after cleaning without being removed from the bed. It should be observed that it is easier for the patient to roll over than to have a complete and new base sheet installed. It can be noted that frame 31 can be raised along elongated areas 46, 47, 48 and 49 of the perimeter of frame 31, thus allowing for access to the base sheet 30 for hygienic cleaning with a disinfectant at bedside.

Instead of requiring unpinning and repinning procedures of the prior art, a soiled disposable underpad may be readily removed from the peripheral groove between the frame 31 and the plastic base 20 by a conscious force involving simple inward sliding of the peripheral portion of the soiled underpad 51 from a portion of the peripheral groove and a fresh disposable underpad can be inserted in tucked, flat, unwrinkled relation within the portion of the peripheral groove vacated by the soiled underpad. These steps are repeated for different portions of the groove until the soiled underpad is removed from all portions of the inwardly facing peripheral groove and replaced in all said groove portions by a fresh underpad If an occupant cannot be removed from the bed, it is a simple matter to roll the occupant in one direction to install one side of the fresh disposable underpad in a flat unwrinkled condition by tucking said one side within the groove and then to roll the occupant in the opposite direction over the partly installed underpad to tuck in the remainder of the underpad within the remainder of the groove.

In use, when a new patient is in the bed, a new underpad holder 10 is employed on the bed. Inserted into the continuous groove formed under the inner marginal portion of frame 31 of underpad holder is a disposable underpad 51 with the periphery of the underpad closely spaced from the bonded outer portion of frame 31. The underpad holder has an inner unbonded portion of frame 31 of sufficient width that overlaps the entire margin of the underpad so that it prevents and minimizes the disposable underpad from moving around and avoids having the marginal portion of the underpad released from its overlapping relation below frame 31 as the patient turns in bed. The underpad holder 10 being made of plastic can be re-used with the same patient and is disposed of after use by said patient is ended. Each new patient receives a new underpad holder.

The peripherally extending, inwardly facing groove formed between the elongated areas 46, 47, 48 and 49 of the frame 31 and the base sheet 30 is completely uninterrupted, even at the four corner portions. This freedom from interruption, such as would result from the presence of pins at each of the corners, makes it possible to insert the entire peripheral portion of a disposable underpad within the entire extent of the peripherally extending, inwardly facing groove in a flat unwrinkled condition tucked between the frame 31 and the base sheet 30 including all four corner portions of the frame. Once the disposable underpad 51 is tucked within frame 31 in flat unwrinkled condition, it is not necessary to pin the underpad 51 to any portion of the underpad holder to maintain the underpad in its desired position. The overlapping of the frame insures that the underpad does not move relative to the frame. In addition, the weight of a bed occupant when the latter is on the bed further insures no movement of the underpad until its removal is desired even when the occupant moves. Then, a conscious positive force is need to separate the pad from the peripherally extending inwardly facing groove.

The bonding between the outer marginal portion of the frame 31 and the upper surface of the plastic base sheet 30 improves the rigidity of the plastic base sheet in the region of heat bonding. Therefore, plastic base sheet 30 tends to remain unwrinkled. The disposable underpad is tucked in unwrinkled relation within the inwardly facing, uninterrupted peripheral groove formed under the inner peripheral portion of frame 31. The dimensions of frame 31 are so related to the dimensions of the disposable underpad 51 that even when two consecutive sides of the underpad 51 abut the bonded outer peripheral edge portion of frame 31 that sufficient overlap remains below the free inner edge portion of the frame 31 over the entire marginal portion of the disposable underpad that the latter remains in fixed position within the uninterrupted peripheral groove until such time as a conscious effort is made to remove a soiled underpad. The free inner marginal edge portion of the frame is also free of wrinkles when an underpad is inserted thereunder and within the continuous, uninterrupted peripheral groove. The lack of wrinkles and the thinness of the frame 31 cause a minimum of discomfort to an occupant of the bed.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense, except as set forth in the following appended claims.

What is claimed is:

1. An underpad holder for use in combination with a disposable underpad and bedding mattress, said holder comprising, in combination, a plastic base sheet having a length longer than the width of a bed and mattress to which said base sheet is adapted to be applied tightly and with the opposite ends of said plastic base sheet folded around the side edges of the mattress and extending laterally inwardly below said mattress and between said mattress and support means provided on said bed to support said mattress, said plastic base sheet having a width extending lengthwise of said bed and mattress sufficient to cover a portion of the length of said bed likely to be soiled by an occupant of said bed, and a disposable underpad on said plastic base sheet, a single layer, continuous, thin, closed frame having a width extending transverse to the perimeter of said frame, said width defining an outer edge portion larger than said disposable underpad and an inner edge portion smaller than said disposable underpad, said outer edge portion having a pair of opposite outer side edges substantially coextensive with opposite outer side edges of a portion of said plastic base sheet disposed centrally of the lateral dimension of said bed and mattress and also having a pair of outer end edges extending transversely of said opposite outer side edges parallel to the opposite sides of said bed and mattress, means to bond said outer edge portion of said continuous frame to the upper surface of said plastic base sheet while keeping said inner edge portion of said continuous frame free of attachment or bonding to said plastic base sheet and to define a peripherally extending inwardly facing groove free of any interruption between the inner edge portion of said continuous frame and said plastic base sheet adapted to receive the entire perimeter portion of said disposable underpad including all corners of said perimeter portion in flat unwrinkled tucked relation within said peripherally extending groove and to remain in said tucked relation without requiring pinning between said underpad and said holder until such time as a conscious positive force is applied to remove said underpad from said tucked relation.

2. The underpad holder of claim 1, further characterized by means to ventilate said base sheet comprising a series of small perforations in said base sheet.

3. The underpad holder of claim 1, further characterized by said outer edge portion of said frame being bonded to said plastic base sheet by heat sealing in a manner to avoid wrinkling of said heat bonded plastic base sheet.

4. The underpad holder of claim 1, wherein the dimensions of said frame are so related to the dimensions of said disposable underpad that the latter can be inserted beneath said frame without wrinkling and have the frame provide sufficient overlap throughout the entire marginal portion of said underpad without requiring any further holding force, yet said underpad can be readily removed from beneath said inner edge portion of said frame when said underpad becomes soiled.

* * * * *